United States Patent [19]
Reichenbach et al.

[11] Patent Number: 5,947,933
[45] Date of Patent: Sep. 7, 1999

[54] SYRINGE HAVING SAFETY SHIELD

[75] Inventors: Eric P. Reichenbach, Pompton Plains; Robert B. Odell, Franklin Lakes; Chad H. Smith, Oak Ridge; Robyn L. Tucker, Ridgewood, all of N.J.

[73] Assignee: Becton, Dickinson and Company, Franklin Lakes, N.J.

[21] Appl. No.: 09/163,790

[22] Filed: Sep. 30, 1998

[51] Int. Cl.⁶ ........................................ A61M 5/00
[52] U.S. Cl. ...................... 604/198; 604/192; 604/263
[58] Field of Search .................... 604/195, 198, 604/192, 187, 110, 263; 128/919

[56] References Cited

U.S. PATENT DOCUMENTS

| | | | |
|---|---|---|---|
| 4,425,120 | 1/1984 | Sampson et al. | 604/198 |
| 4,573,976 | 3/1986 | Sampson et al. | 604/198 |
| 4,631,057 | 12/1986 | Mitchell | 604/198 |
| 4,702,738 | 10/1987 | Spencer | 604/198 |
| 4,723,943 | 2/1988 | Spencer | 604/198 |
| 4,737,144 | 4/1988 | Choksi | 604/198 |
| 4,747,837 | 5/1988 | Hauck | 604/198 |
| 4,801,295 | 1/1989 | Spencer | 604/198 |
| 4,874,383 | 10/1989 | McNaughton | 604/198 |
| 5,154,698 | 10/1992 | Compagnucci et al. | 604/110 |
| 5,222,945 | 6/1993 | Basnight | 604/110 |
| 5,304,149 | 4/1994 | Morigi | 604/192 |
| 5,338,310 | 8/1994 | Lewandowski | 604/192 |
| 5,342,309 | 8/1994 | Hausser | 604/110 |
| 5,385,555 | 1/1995 | Hausser | 604/192 |
| 5,573,514 | 11/1996 | Stiehl et al. | 604/198 |
| 5,647,849 | 7/1997 | Kalin | 604/192 |
| 5,658,254 | 8/1997 | Reichenbach et al. | 604/192 |
| 5,674,203 | 10/1997 | Lewandowski | 604/197 |

*Primary Examiner*—John D. Yasko
*Attorney, Agent, or Firm*—John L. Voellmicke

[57] ABSTRACT

A hypodermic syringe assembly is provided with a syringe barrel and a safety shield telescoped over the syringe barrel and movable from a proximal position to a distal position. The safety shield is irreversibly lockable in the distal position on the syringe barrel to protectively shield a used needle cannula. The safety shield is releasably retained in a proximal position by engagement of a protrusion on the barrel and a groove on the shield. Engagement between the protrusion and the stop block can be overcome by rotating the safety shield. The safety shield may then be moved into an irreversible shielding position surrounding the needle cannula. The releasable retention of the safety shield in its proximal position prevents inadvertent distal movement of the safety shield.

12 Claims, 6 Drawing Sheets

SYRINGE HAVING SAFETY SHIELD

BACKGROUND OF THE INVENTION

1. Field of the Invention

The subject invention relates to an assembly of a syringe barrel, a needle cannula and a safety shield. The safety shield is telescoped over the syringe barrel and is movable between a proximal position where a needle cannula is exposed for use and a distal position where the needle cannula is shielded.

2. Description of the Prior Art

A prior art hypodermic syringe includes an elongate syringe barrel with a proximal end, a distal end and a tubular side wall extending therebetween. The side wall defines a cylindrical fluid receiving chamber within the syringe barrel. The proximal end of the syringe barrel is opened into the fluid receiving chamber. An elongated tip is defined at the distal end of the syringe barrel and has a narrow fluid passage that communicates with the fluid receiving chamber.

The prior art hypodermic syringe also includes a needle cannula with a proximal end, a distal end which is usually sharpened and a lumen extending therethrough. The needle cannula is mounted or mountable to the tip of the syringe barrel such that the lumen through the needle cannula communicates with the fluid receiving chamber in the syringe barrel. Some prior art hypodermic syringes have the proximal end of the needle cannula fixedly and permanently mounted to the tip of the syringe barrel. However, other prior art hypodermic syringes include a needle cannula that is removable mounted to the tip of the syringe barrel. For example, many prior art syringe barrels include an internally threaded luer-type collar surrounding the tip. The proximal end of the needle cannula is mounted to a needle hub which is threadedly engageable with the luer collar and which telescopes over the tip to place the lumen of the prior art needle cannula in communication with the fluid receiving chamber of the prior art syringe barrel.

The prior art hypodermic syringe further includes a plunger slidably disposed within the fluid receiving chamber of the syringe barrel. Distal movement of the plunger in the syringe barrel urges fluid from the chamber and through the needle cannula. Conversely, proximal movement of the plunger in the syringe barrel draws fluid through the needle cannula and into the fluid receiving chamber.

Most prior art hypodermic syringes include structure for preventing accidental sticks. For example, most prior art hypodermic syringes have a rigid cap mounted over the needle cannula prior to use. The rigid cap includes an open proximal end that is removably mounted to either the hub of the needle cannula or to a distal portion of the syringe barrel. The cap is removed immediately prior to use of the hypodermic syringe to expose the needle cannula. However, reshielding a used needle cannula with a prior art cap is not recommended because a misalignment of the cap and the needle cannula during this reshielding operation can result in the accidental stick. As a result, many hypodermic syringes include a safety shield that is intended to enable reshielding.

A prior art hypodermic syringe having a safety needle shield is disclosed in U.S. Pat. No. 5,658,254. This prior art syringe includes a rigid tubular safety shield that is mounted over the syringe barrel and that is movable from a proximal position to a distal position relative to the syringe barrel. The safety shield is dimensioned such that the needle cannula is exposed when the safety shield is in its proximal position on the syringe barrel. However, the dimensions of the safety shield ensure that the needle cannula is protectively surrounded when the safety shield is in a distal position on the syringe barrel. The proximal end of the prior art safety shield has internal cross-sectional dimensions that enable frictional retention of the safety shield in the proximal position. Additionally, the proximal end of the prior art safety shield is configured to lockingly engage structure at the distal end of the syringe barrel. This locking structure is configured to prevent re-exposure of the needle cannula by sliding the safety shield proximally along the syringe barrel.

Releasable retention of the safety shield in the proximal position is necessary to prevent the needle shield from sliding distally into a position where the needle shield interferes with use of the needle cannula. However, a releasable engagement that relies entirely upon a frictional interfit is difficult in view of the close manufacturing tolerances that are required. For example, a frictional interfit that is too tight may make shielding difficult. Conversely, a frictional interfit that is too loose may cause the needle shield to inadvertently slide distally along the syringe barrel while the syringe is being used.

SUMMARY OF THE INVENTION

A shieldable syringe assembly of the present invention includes a syringe barrel having a proximal end, a distal end and a tubular side wall extending between the ends. The barrel includes at least one protrusion comprising a circumferential segment spaced distally from the proximal end of the syringe barrel, and an axial segment preferably extending in a proximal direction from one end of the circumferential segment of the protrusion. A safety shield having proximal and distal ends is also provided. The safety shield is slidably disposed around the syringe barrel and is movable from a proximal position to a distal position relative to the syringe barrel. The safety shield includes at least one stop block projecting inwardly from the proximal end of the safety shield. The stop block is dimensioned to fit between the circumferential segment of the protrusion and the proximal end of the syringe barrel for preventing the safety shield from moving distally from its proximal position, and the axial segment is configured to limit rotational movement of a stop block relative to the syringe barrel. Means for locking the safety shield in the distal position wherein locking engagement can be achieved with only axial movement of the safety shield distally with respect to the barrel is also provided.

Another embodiment of the present invention includes at least one bead between the circumferential segment of the protrusion and the proximal end of the syringe barrel for releasably retaining the stop block in a rotational position aligned with the circumferential segment of the protrusion so that portions of the stop block are releasably retained between the axial segments and the bead to prevent inadvertent axial movement of the safety shield during use of the syringe. The bead may take any shape which will retain the stop block with an axial rib shape being preferred.

Another embodiment of the present invention includes at least one recess in the stop block. The recess is dimensioned for releasable engagement with the bead for releasably retaining the stop block in a rotational position aligned with the circumferential segment of the protrusion so that rotational forces on the safety shield disengage the recess and the bead and move the stop block to a rotational position for distal movement past the protrusion.

In another embodiment of the present invention the circumferential segment of the protrusion includes an angled distal face to help guide the stop block past the protrusion when the shield is being moved to its proximal position. The angled distal face can be an incline, a curvilinear face or a pointed surface to guide the stop block to one of the two sides of the protrusion.

Another embodiment of the present invention includes a plurality of stop blocks in the safety shield and a plurality of protrusions on the syringe barrel.

Another embodiment of the present invention includes a needle cannula mounted on the distal end of the syringe barrel. The cannula may be mounted directly to the syringe barrel or mounted indirectly as part of a needle assembly which includes a hub which is attached to the distal end of the syringe barrel. In either case, the safety shield should have a length sufficient for shielding the needle cannula when the safety shield is in its distal position.

DETAILED DESCRIPTION OF THE PREFERRED EMBODIMENT

Figure 1:
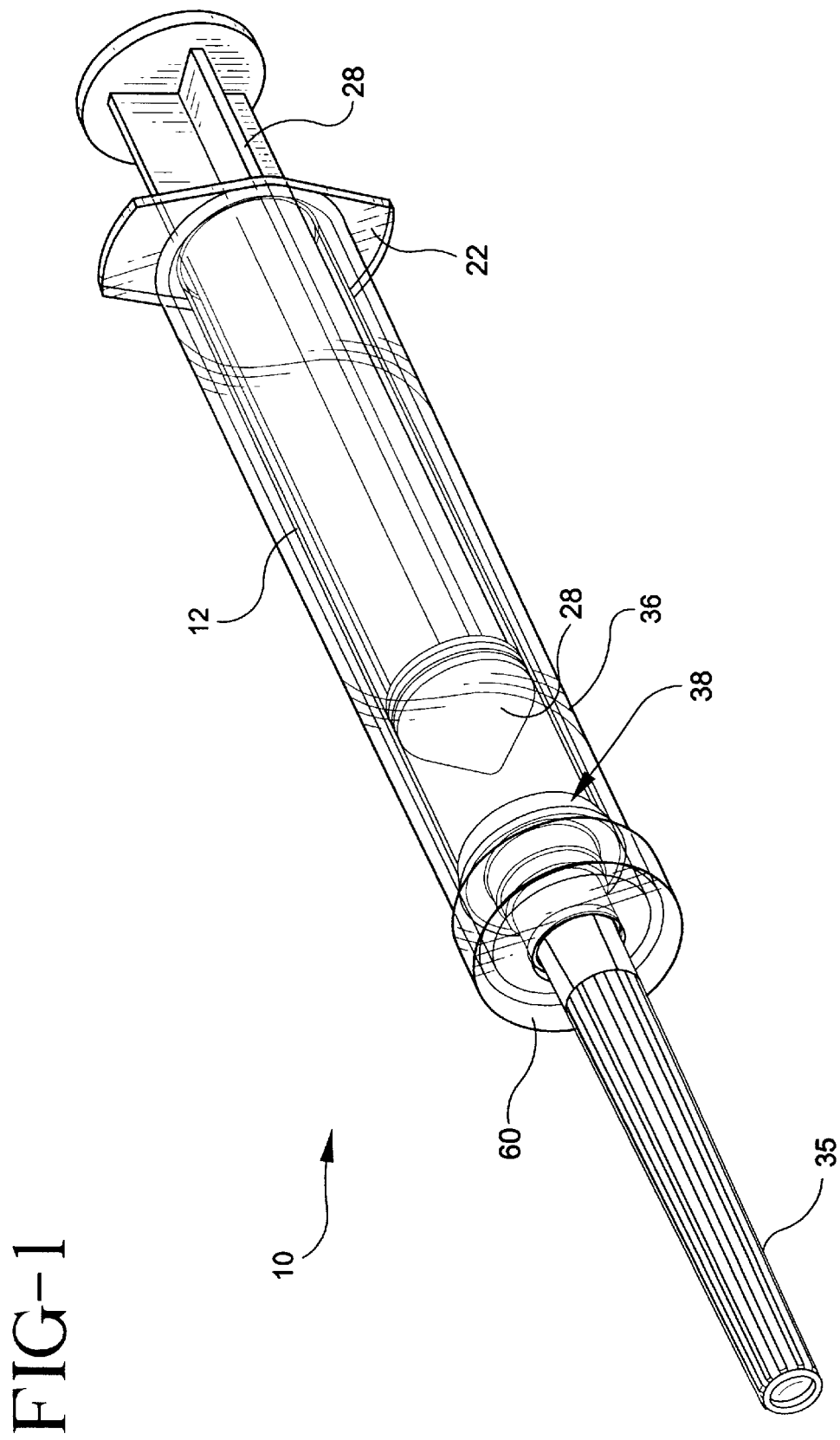
FIG. 1 is a perspective view of a sliding sleeve safety syringe in accordance with the subject invention.
Figure 2:
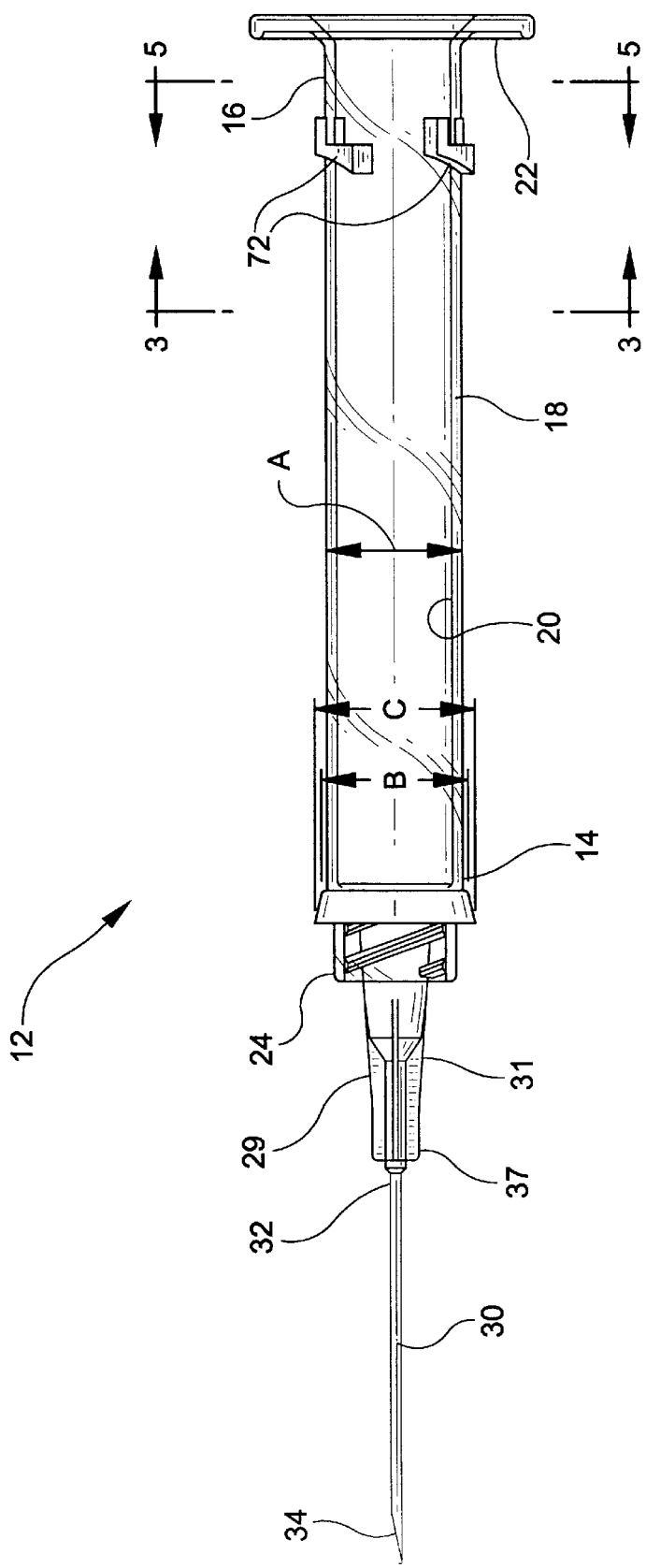
FIG. 2 is a side elevational view of syringe without the needle cover and the safety shield.
Figure 4:
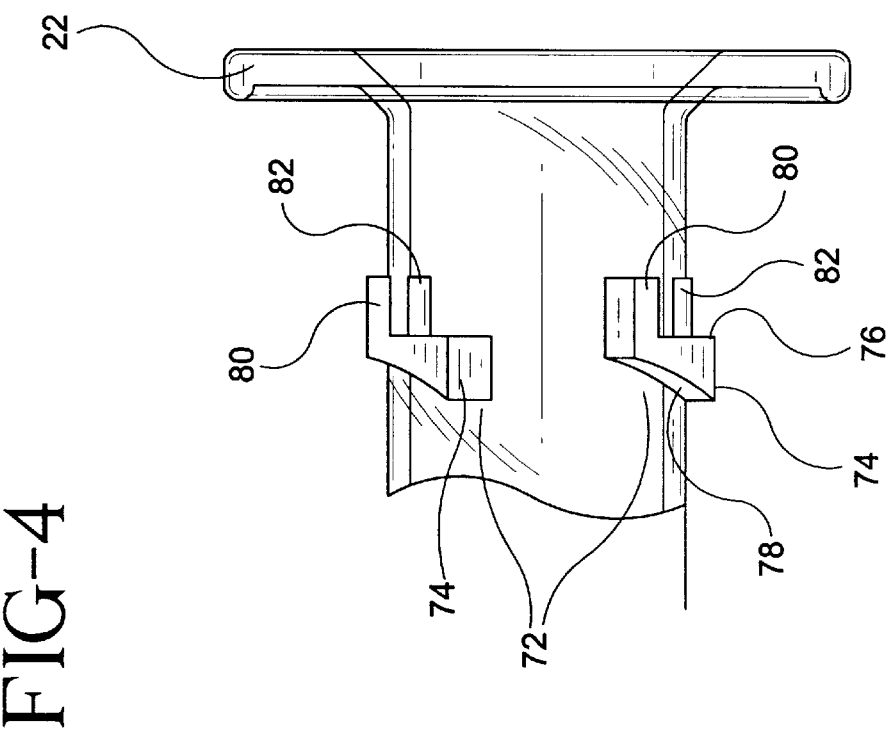
FIG. 4 is an enlarged partial side elevational view of the syringe of FIG. 2.
Figure 3:
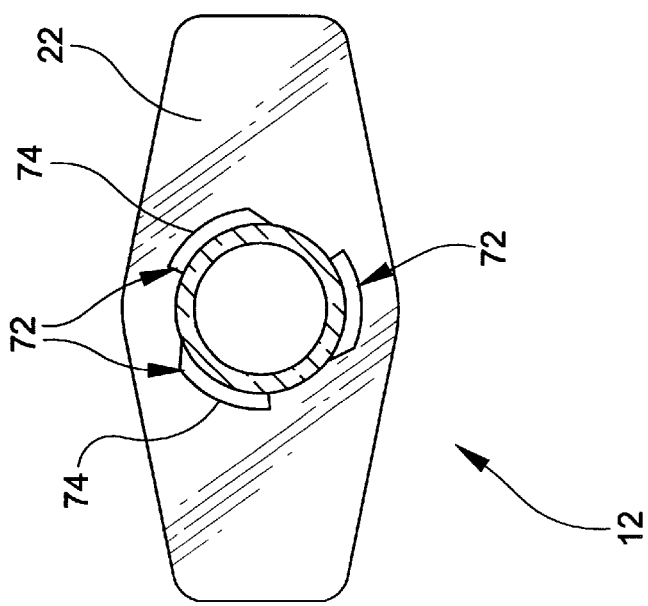
FIG. 3 is a cross-sectional view taken along line 3—3 in FIG. 2.
Figure 6:
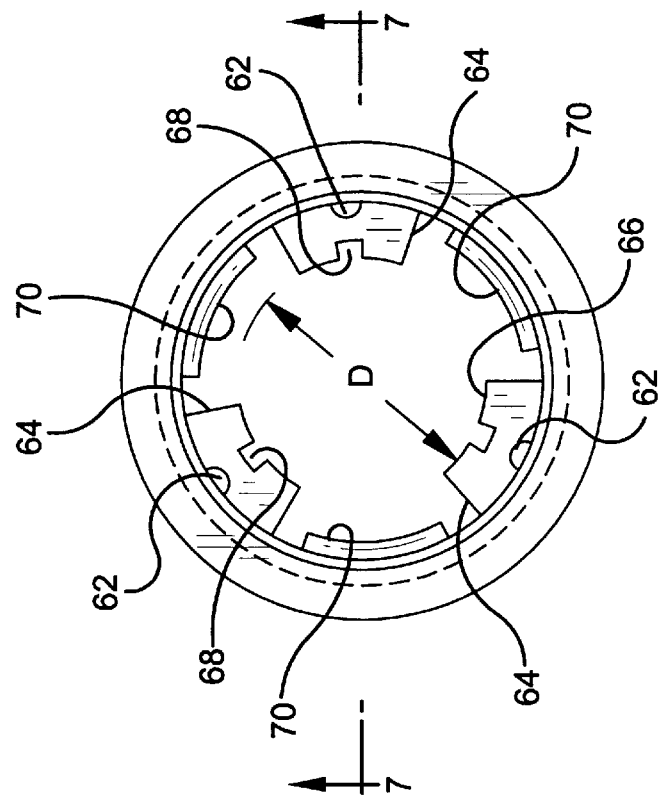
FIG. 6 is an end view of the distal end of the safety shield.
Figure 5:
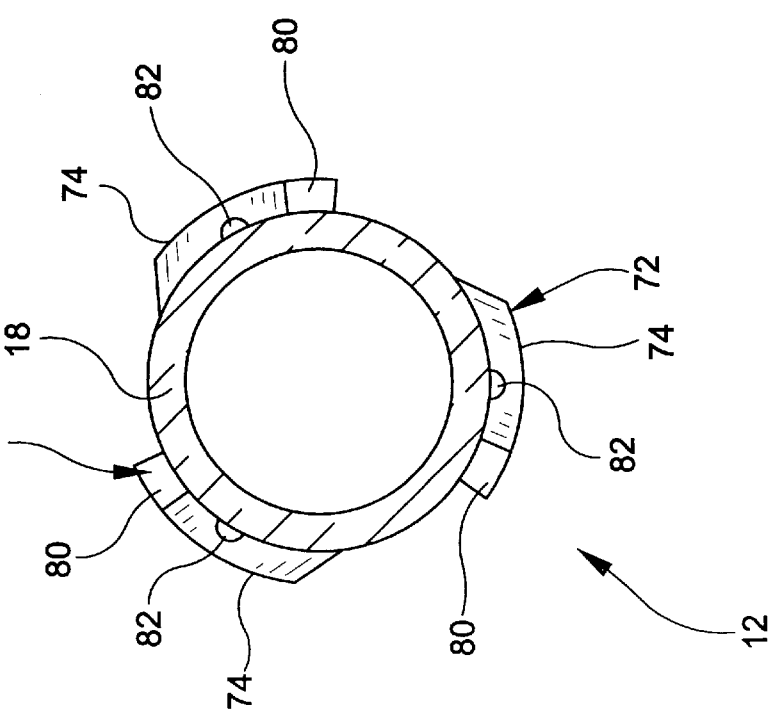
FIG. 5 is a cross-sectional view taken along line 5—5 in FIG. 2.
Figure 7:
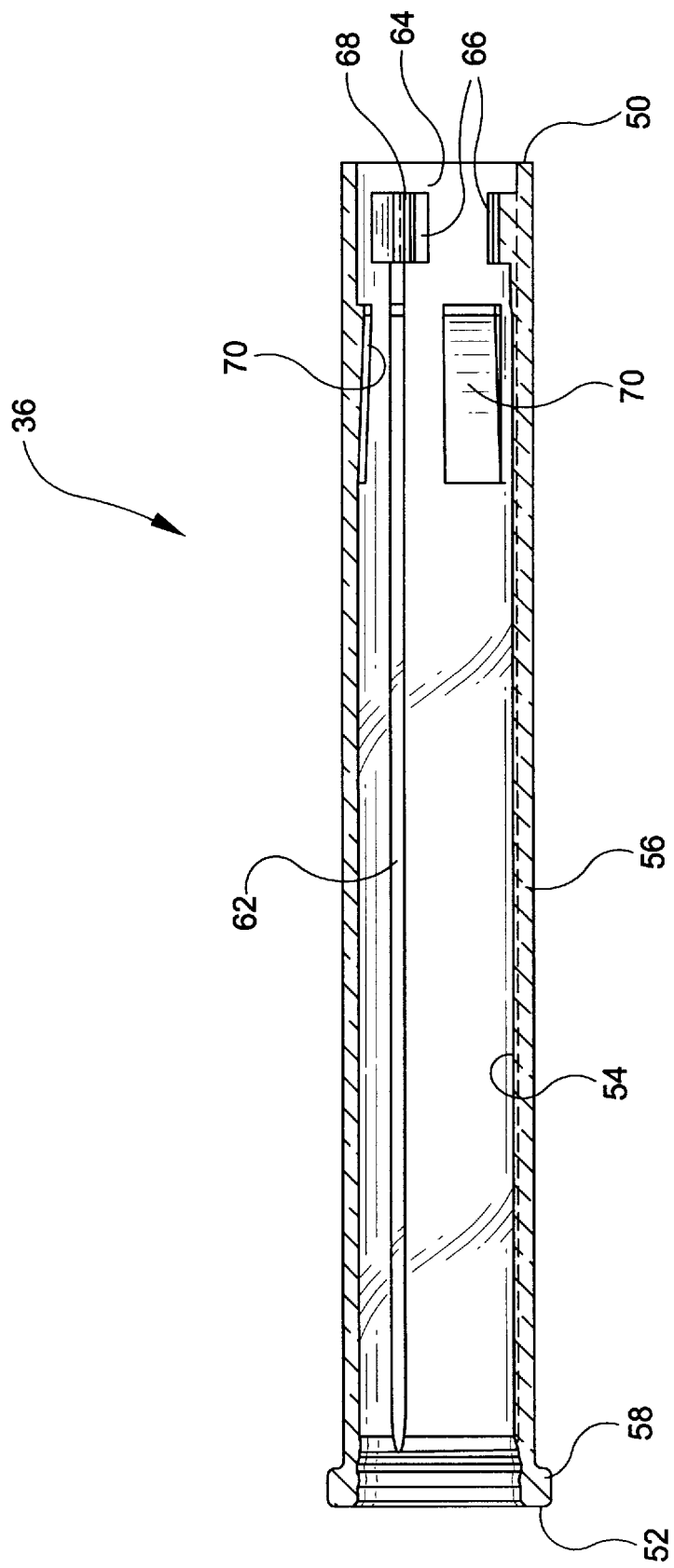
FIG. 7 is a cross-sectional view taken along line 7—7 in FIG. 6.
Figure 8:
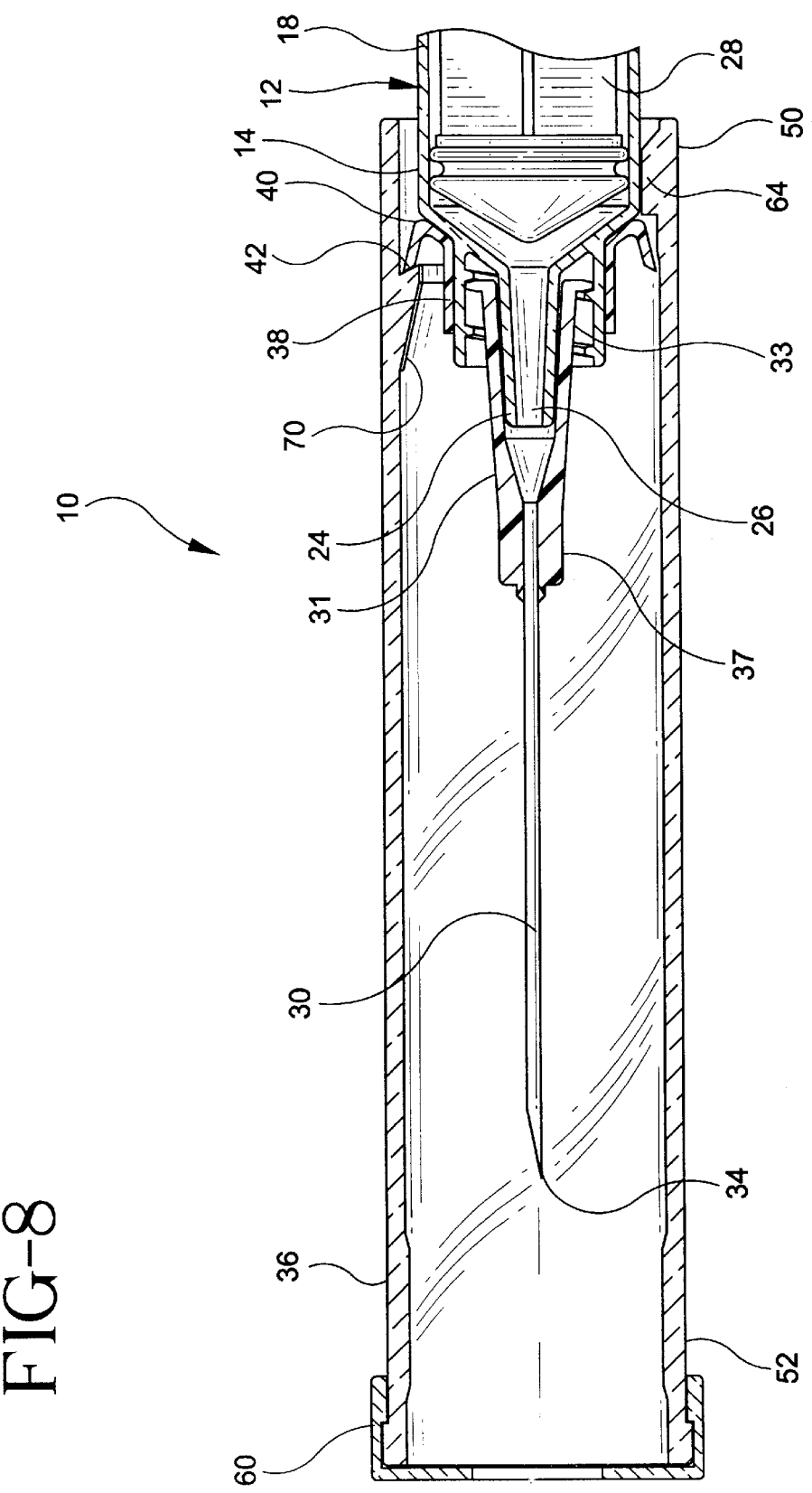
FIG. 8 is a cross-sectional view of the sliding sleeve safety syringe with the safety sleeve in its distal needle protecting position.

Referring to FIGS. 1–8, a syringe assembly in accordance with the subject invention is identified generally by the numeral 10. Syringe assembly 10 includes a syringe barrel 12 having a distal end 14, an open proximal end 16 and a generally cylindrical wall 18 extending between the ends to define a fluid receiving chamber 20. Cylindrical wall 18 of syringe barrel 12 defines an outside diameter "A" along much of its length. An outwardly projecting finger flange 22 is defined near proximal end 16 of the syringe barrel for facilitating digital manipulation of syringe assembly 10. Additionally, distal end 14 of syringe barrel 12 is characterized by a tip 24. Tip 24 is provided with a fluid passage 26 extending therethrough and communicating with fluid receiving chamber 20.

A plunger 28 is disposed in fluid receiving chamber 20 and is in sliding fluid-tight engagement with cylindrical wall 18 of syringe barrel 12. Sliding movement of plunger 28 in a distal direction causes fluid in chamber 20 to be expelled through passage 26 of tip 24. Conversely, sliding movement of plunger 28 in a proximal direction draws fluid through passage 26 and into fluid receiving chamber 20.

A needle assembly 29 is connected to tip 24. More particularly, the needle assembly includes needle cannula 30 having a proximal end 32, a sharp distal end 34 and a lumen extending therebetween. A hub 31 having an open proximal end 33 and a distal end 37 is joined to the proximal end of the cannula so that the lumen is in fluid communication with the open proximal end of the hub. Tip 24 fits into open proximal end 33 of the hub and frictionally engages the hub so that the lumen of needle cannula 30 communicates with passage 26 through tip 24 and further communicates with fluid receiving chamber 20 of syringe barrel 12. In this embodiment, needle assembly 29 is removably mounted to tip 24. However, it is within the purview of the present invention to include a needle cannula that is directly and permanently mounted to the syringe tip.

A needle cover 35 is removably mounted over needle cannula 30 to prevent accidental sticks prior to use of syringe assembly 10. Needle cover 35 can be removed from syringe assembly 10 immediately prior to use.

Syringe assembly 10 is provided with a rigid safety shield 36 and an annular collar 38 for locking the shield in its proximal needle protecting position. Collar 38 is preferably formed from a plastic material and is configured for mounting around tip 24 of syringe barrel 12. More particularly, collar 38 includes a proximal end 40 and a distal end 42. Collar 38 includes a generally frustom shaped outer surface that expands to greater diameters at locations closer to distal end 42 of collar 38. Proximal end 40 of collar 38 defines an outside diameter "B" that is slightly greater than outside diameter "A" of cylindrical wall 18 of syringe barrel 12. Distal end 42 of collar 38 defines an outside diameter "C" which is greater than outside diameter "B" of proximal end 40 of the collar. As explained further below, the shape and dimensions of collar 38 cooperate with structure on safety shield 36 for substantially permanently shielding needle cannula 32 after use.

Safety shield 36 is a rigid preferably cylindrical tube having a proximal end 50, a distal end 52 and a length greater than the length of needle cannula 30. Safety shield 36 includes inner and outer substantially cylindrical surfaces 54 and 56 respectively. Portions of outer surface 56 near distal end 52 are characterized by a circumferentially enlarged portion 58 to which an annular cap 60 may be affixed. Annular cap 60 permits passage of needle cannula 30 but prevents insertion of a finger.

Inner circumferential surface 54 of safety shield 36 include three equally spaced ridges 62 extending axially therealong. Innermost portions of ridges 62 define a locus of points on a cylinder having a diameter slightly greater than the outer diameter "A" of syringe barrel 12. Thus, ridges 62 maintain substantially coaxially alignment between syringe barrel 12 and safety shield 36. Ridges 62 further avoid binding that could occur if the respective axes of syringe barrel 12 and safety shield 36 were significantly skewed or if there were close dimensional tolerances between inner and outer circumferential surfaces.

Portions of inner circumferential surface 54 of safety shield 36 adjacent proximal end 50 include three equally spaced stop blocks 64. Stop blocks 64 have an inner circumferential surfaces 66 which define a portion of a cylinder of diameter "D" which is slightly greater than outside diameter "A" of syringe barrel 12 but less than the minimum side diameter "B" of collar 38. Stop blocks 64 are sufficiently long and rigid to resist forces generated as safety shield 36 is moved distally along syringe barrel 12 and into collar 38 as explained herein. Each stop block 64 preferably includes a groove 68 extending axially along inner circumferential surface 66.

Inner circumferential surface 62 of safety shield 36 is characterized further by three locking teeth 70 which are rotationally disposed to lie intermediate angular positions of stop blocks 64. Thus, as shown most clearly in FIG. 7, stop blocks 64 and locking teeth 70 are alternately arranged relative to one another around the inner circumference of safety shield 36. Locking teeth 70 are spaced distally from stop blocks 64 by an axial distance that is equal or greater than the distance between proximal and distal ends 40 and 42 of collar 38. Additionally, locking teeth 70 are tapered so that proximal ends of locking teeth 70 define arcs of a circle having a diameter less than the maximum outside diameter "C" of collar 38. However, distal ends of locking teeth 70 merge into remaining portions of inner cylindrical surface 54 of safety shield 36. This ramped configuration functions to deflect collar 38 radially inwardly and/or to deflect safety shield 36 outwardly in response to distal movement of safety shield 36 along syringe barrel 12. However, after sufficient distal movement of safety shield 36 along syringe barrel 12, collar 38 will lie between stop blocks 64 and locking teeth 70. The above-described cooperation of collar 38 with stop blocks 64 and locking teeth 70 prevents a proximal movement of safety shield 36 that would re-expose a previously used needle cannula.

It is also desirable to prevent an inadvertent distal movement of safety shield 36 while it is in its proximal needle exposing position, so that the safety shield does not interfere with normal usage of needle cannula 30. For this purpose, outer circumferential surface 18 of syringe barrel 12 is provided with at least one and preferably more than one equally spaced protrusions 72 in proximity to finger flange 22. Each protrusion 72 includes a circumferential segment 74 that is spaced distally from flange 22 by a distance slightly greater than the axial dimension of stop blocks 64. Thus, stop blocks 64 can be positioned between circumferential segments 74 of protrusions 72 and finger flange 22 to prevent an inadvertent distal movement of safety shield 36. Circumferential segments 74 of protrusions 72 include proximal faces 76 that lie in a common radially extending plane spaced distally from finger flange 22 by a distance that exceeds the axial length of stop blocks 64. Circumferential segments 74 of protrusions 72 further include angled distal faces 78. Angled distal faces 78 do not lie in a common radial plane. Thus, distal faces 78 of circumferential segments 74 function as cams which engage proximal faces of stop blocks 64 during proximal movement of safety shield 36. Stop blocks 64 are guided along the cam surfaces of circumferential segment 74 and into alignment with spaces between protrusions 72 to ensure maximum proximal movement of safety shield 36 along syringe barrel 12.

Each protrusion 72 further includes an axial segment 80 preferably extending from one end of circumferential segment 74 toward finger flange 22. Axial segments 80 limit rotational movement of stop blocks 64 relative to syringe barrel 12 and thereby prevent over rotation of safety shield 36 beyond a position where stop blocks 64 align with circumferential segments 74 of protrusions 72.

Releasable retention of safety shield 36 in its proximal needle exposing position is ensured by beads such as retention ribs 82 which preferably extend axially between finger flange 22 and proximal face 76 of circumferential segments 74 on protrusions 72. Retention ribs 82 are dimensioned and disposed to be engaged releasably in grooves 68 of stop blocks 64. Ribs 82 are spaced from axial segments 80 of protrusions 72 by a sufficient distance to receive portions of surfaces 66 of stop blocks 64.

Safety shield 36 is placed in its releasable retention position by first moving safety shield 36 to its extreme proximal position such that proximal ends of stop blocks 64 are substantially adjacent finger flange 22. Safety shield 36 then is rotated such that stop blocks 64 move into positions between finger flange 22 and circumferential segments 74 of protrusions 72. Rotation of safety shield 36 is limited by engagement between stop blocks 64 and axial segment 80 of protrusions 72. Retention ribs 82 will snap into grooves 68 of lock block 64 substantially when lock block 64 reach their rotational limit adjacent axial segments 80 of protrusions 72. Thus, over rotation of safety shield is prevented by axial segments 80 of protrusions 72, while inadvertent return rotational movement is prevented by engagement of retention ribs 82 in grooves 68. It should be noted that grooves 68 are not necessary to practice the present embodiment. The stop blocks can be dimensioned more narrowly so that upon rotation of the safety shield the stop blocks will fit between axial segment 80 of protrusions 72 and retention ribs 82 to releasably retain the safety shield in its proximal position.

After use, safety shield 36 can be moved into a shielded position by rotating safety shield 36 with sufficient force to overcome engagement between retention ribs 82 and grooves 68 or the retention ribs and the stop blocks if grooves are not provided. Over rotation is prevented when stop blocks 64 engage the next sequential protrusion 72. At this point, safety shield 36 can be moved distally to its extreme distal needle protecting position such that collar 38 is lockingly engaged between stop block 64 and locking teeth 70. Further distal movement is prevented by engagement of lock blocks 64 with collar 38, while a return proximal movement that could re-expose the used needle cannula is prevented by engagement of locking teeth 70 with collar 38.

What is claimed is:

1. A shieldable syringe assembly comprising:
    a syringe barrel having a proximal end, a distal end and a tubular side wall extending between said ends, at least one protrusion comprising a circumferential segment spaced distally from said proximal end of said syringe barrel, and an axial segment extending proximally from one end of said circumferential segment of said protrusion,
    a safety shield having proximal and distal ends, said safety shield being slidably disposed around said syringe barrel and being movable from a proximal position to a distal position relative to said syringe barrel, at least one stop block projecting inwardly from said proximal end of said safety shield, said stop block being dimensioned to fit between said circumferential segment of said protrusion and said proximal end of said syringe barrel and to prevent said safety shield from moving distally from said proximal position, and said axial segment being configured to limit rotational movement of said stop block relative to said syringe barrel; and
    means for locking said safety shield in said distal position wherein locking engagement can be achieved with only axial movement of said safety shield distally with respect to said barrel.

2. The assembly of claim 1, wherein said syringe barrel includes an outwardly extending flange at said proximal end for limiting proximal movement of said safety shield on said syringe barrel and defining a proximal extreme position of said safety shield on said syringe barrel.

3. The assembly of claim 1, wherein the circumferential segment of said protrusion includes a proximal face aligned in a substantially radial direction relative to said syringe barrel.

4. The assembly of claim 1, wherein the circumferential segment of the protrusion includes an angled distal face to help guide said stop block past said protrusion when said shield is being moved in a proximal direction.

5. The assembly of claim 1, wherein said at least one stop block comprises a plurality of spaced stop blocks, and wherein said at least one protrusion comprises a plurality of spaced protrusions, said stop blocks being dimensioned to move axially between said protrusions.

6. The assembly of claim 1 further including at least one bead between said circumferential segment of said protrusion and said proximal end of said syringe barrel for releasably retaining said stop block in a rotational position aligned with said circumferential segment of said protrusion.

7. The assembly of claim 6 wherein said stop block further includes at least one recess disposed and dimensioned for releasable engagement with said bead for releasably retaining said stop block in a rotational position aligned with said circumferential segment of said protrusion, whereby rotational forces on said safety shield disengage said recess and said bead and move said stop block to a rotational position for distal movement past said protrusion.

8. The assembly of claim 7, wherein said bead is an axially extending rib, and wherein said recess is an axially extending groove.

9. The assembly of claim 1, further comprising a needle cannula mounted to said distal end of said syringe barrel, said safety shield having a length sufficient for shielding said needle cannula when said safety shield is in said distal position.

10. A shieldable syringe assembly comprising:

a syringe barrel having a proximal end, a distal end and a tubular side wall extending between said ends, a plurality of protrusions projecting outwardly on said syringe barrel, each said protrusion including an axial segment projecting axially on said syringe barrel and a circumferential segment projecting circumferentially from a location on said axial segment spaced from said proximal end of said syringe barrel, at least one axial aligned bead extending proximally from at least one of said circumferential segments of said protrusions; and a safety shield having proximal and distal ends, said safety shield being slidably disposed around said syringe barrel and being movable from a proximal position to a distal position on said syringe barrel, a plurality of stop blocks projecting inwardly from said proximal end of said safety shield, said stop blocks being dimensioned to fit between said circumferential segments of said protrusions and said proximal end of said syringe barrel and further being dimensioned to prevent said safety shield from moving distally from said proximal position on said syringe barrel, at least one of said stop blocks having at least one axial aligned recess disposed and dimensioned for releasable engagement with said bead for releasably retaining said stop block in a rotational position aligned with said circumferential segment of said protrusion, whereby rotation forces on said safety shield disengage said recess and said bead and move said stop lock rotationally into a position for distal movement passed said protrusion.

11. The assembly of claim 10, wherein said syringe barrel includes an outer circumferential surface, said protrusion projecting a selected radial distance from said outer circumferential surface, said bead projecting a selected radial distance from said outer circumferential surface that is less than the radial projection of said protrusion.

12. The assembly of claim 11, wherein the circumferential segment of each said protrusion comprises a proximal face, said proximal faces of said protrusions lying in a common radial aligned plane, the circumferential segment of each said protrusion further having a distal face aligned at an angle to the respective proximal face of said protrusion.

\* \* \* \* \*